(12) United States Patent
Ghajar

(10) Patent No.: US 7,708,700 B2
(45) Date of Patent: May 4, 2010

(54) TRAINING SYSTEM AND METHOD FOR IMPROVING COGNITION AND MOTOR TIMING

(76) Inventor: Jamshid Ghajar, 110 E. 71st St., #3, New York, NY (US) 10021

(*) Notice: Subject to any disclaimer, the term of this patent is extended or adjusted under 35 U.S.C. 154(b) by 0 days.

(21) Appl. No.: 12/118,468

(22) Filed: May 9, 2008

(65) Prior Publication Data

US 2008/0206727 A1    Aug. 28, 2008

Related U.S. Application Data

(62) Division of application No. 10/834,356, filed on Apr. 27, 2004, now Pat. No. 7,384,399.

(51) Int. Cl.
| | |
|---|---|
| A61B 13/00 | (2006.01) |
| A61B 5/00 | (2006.01) |
| A61B 5/04 | (2006.01) |
| A61B 5/05 | (2006.01) |
| A61B 5/103 | (2006.01) |
| A61B 5/117 | (2006.01) |
| G06K 9/00 | (2006.01) |
| G08B 21/00 | (2006.01) |
| G08B 23/00 | (2006.01) |

(52) U.S. Cl. .................. 600/558; 600/300; 600/301; 600/544; 600/545; 600/546; 600/547; 600/587; 600/595; 600/559; 128/920; 128/922; 128/923; 128/924; 128/925; 382/100; 382/110; 382/115; 382/117; 340/540; 340/573.1; 340/576

(58) Field of Classification Search .............. 600/300, 600/301, 544, 545, 546, 547, 558, 587, 595, 600/559; 351/200, 201, 203, 205, 206; 128/920, 128/922, 923, 924, 925; 382/100, 110, 115, 382/117; 340/540, 573.1, 576

See application file for complete search history.

(56) References Cited

U.S. PATENT DOCUMENTS 4,332,566 A    6/1982    Mazeski et al. ............. 434/178

(Continued)

OTHER PUBLICATIONS

Ball et al., "The Role of Higher-Order Motor Areas in Voluntary Movement as Revealed by High-Resolution EEG and fMRI," NeuroImage, (1999) 10:682-694.

(Continued)

Primary Examiner—Max Hindenburg
Assistant Examiner—Jeffrey G Hoekstra
(74) Attorney, Agent, or Firm—Morgan, Lewis & Bockius LLP

(57) ABSTRACT

A method of training a subject to improve anticipatory timing includes presenting the subject with multiple sequences of stimuli, receiving sensor signals associated with responses by the subject to the stimuli, and recording response times in accordance with the sensor signals, wherein the recorded response times are associated with the responses by the subject to the multiple sequences of stimuli, and wherein the response times have an associated distribution. The method further includes analyzing the distribution of response times for the subject to determine variability in anticipatory timing of the subject with respect to the stimuli, and generating a subject feedback signal corresponding to a result of the analyzing so as to train the subject to improve anticipatory timing of the subject. Also disclosed is a system for performing the aforementioned training method.

7 Claims, 6 Drawing Sheets

U.S. PATENT DOCUMENTS

| | | | | |
|---|---|---|---|---|
| 4,838,681 | A | 6/1989 | Pavlidis | 351/210 |
| 4,889,422 | A | 12/1989 | Pavlidis | 351/210 |
| 5,137,027 | A | 8/1992 | Rosenfeld | 128/731 |
| 5,331,969 | A | 7/1994 | Silberstein | 128/731 |
| 5,491,492 | A | 2/1996 | Knapp et al. | 345/8 |
| 5,529,498 | A | 6/1996 | Cassily et al. | 434/258 |
| 5,662,117 | A | 9/1997 | Bittman | 128/732 |
| 5,743,744 | A | 4/1998 | Cassily et al. | 434/258 |
| 5,867,587 | A | 2/1999 | Aboutalib et al. | 382/117 |
| 6,090,051 | A | 7/2000 | Marshall | 600/558 |
| 6,102,870 | A | 8/2000 | Edwards | 600/558 |
| 6,162,186 | A | 12/2000 | Scinto et al. | 600/558 |
| 2002/0099305 | A1 | 7/2002 | Fukushima et al. | 600/558 |

OTHER PUBLICATIONS

Barnes, et al., "Anticipatory Control of Hand and Eye Movements in Humans During Oculo-Manual Tracking," *J. of Physiology*, (2002) 539.1:317-330.

Chan et al., "Are There Sub-types of Attentional Deficits in Patients with Persisting Post-Concussive Symptoms? A Cluster Analytical Study," *Brain Injury* (2003) 17(2):131-148.

Gibbon et al., "Toward a Neurobiology of Temporal Cognition: Advances and Challenges," *Current Opinion in Neurobiology*, (1997) 7:170-184.

Gredeback, G., et al., "The Development of Two-Dimensional Tracking: A Longitudinal Study of Circular Pursuit," Experimental Brain Research, vol. 163, No. 2, May 2005, pp. 204-213.

Green et al., "Deficits in Facial Emotion Perception in Adults with Recent Traumatic Brain Injury," *Neuropsychologia*, (2004) 42:133-141.

Hulsmann et al., "From Will to Action: Sequential Cerebellar Contributions to Voluntary Movement," *NeuroImage*, (2003) 20:1485-1492.

Kathmann, N., et al., "Deficits in Gain of Smooth Pursuit Eye Movements in Schizophrenia and Affective Disorder Patients and Their Unaffected Relatives," The American Journal of Psychiatry, vol. 160, No. 4, Apr. 2003, pp. 696-702.

Lewine et al., "Neuromagnetic Assessment of Pathophysiologic Brain Activity Induced by Minor Head Trauma," *AJNR Am. J. Neuroradiol.*, (May 1999) 20:857-866.

Lutz et al., "Guiding the Study of Brain Dynamics by Using First-Person Data: Synchrony Patterns Correlate with Ongoing Conscious States During a Simple Visual Task," *PNAS*, (Feb. 5, 2002) 99(3):1586-1591.

Madelain et al., "Effects of Learning on Smooth Pursuit During Transient Disappearance of a Visual Target," *J. Neurophysiol.*, (2003) 90:972-982.

Mangels et al., "Effects of Divided Attention on Episodic Memory in Chronic Traumatic Brain Injury: A Function of Severity and Strategy," *Neuropsychologia*, (2002) 40:2369-2385.

Mehta et al., "Forward Models in Visuomotor Control," *J. Neurophysiol.*, (2002) 88:942-953.

Pedersen et al., "Origin of Human Motor Readiness Field Linked to Left Middle Frontal Gyrus by MEG and PET," *NeuroImage*, (1998) 8:214-220.

Perbal et al., "Relationships Between Time Estimation, Memory, Attention, and Processing Speed in Patients with Severe Traumatic Brain Injury ," *Neuropsychologica*, (2003) 41:1599-1610.

Smith et al., "A Right Hemispheric Frontocerebellar Network for Time Discrimination of Several hundreds of Milliseconds," *NeuroImage*, (2003) 20:344-350.

Strauss et al., "Intraindividual Variability in Cognitive Performance in Three Groups of Older Adults: Cross-domain Links to Physical Status and Self-Perceived Affect and Beliefs," *J. of the International Neuropsychol. Soc.*, (2002) 8:893-906.

TRAINING SYSTEM AND METHOD FOR IMPROVING COGNITION AND MOTOR TIMING

This application is a divisional patent application of U.S. patent application Ser. No. 10/834,356, "Cognition and Motor Timing Diagnosis and Training System and Method," filed Apr. 27, 2004, now U.S. Pat. No. 7,384,399 which is hereby incorporated by reference.

TECHNICAL FIELD

The disclosed embodiments relate generally to systems and methods of testing a person's ability to anticipate stimuli, as well as remedial systems and methods for improving a person's ability to accurately anticipate the timing of predictable events or stimuli.

BACKGROUND

Anticipation or expectation of a sensory event that must be paired with an action is essentially a form of attention that is crucial for an organism's interaction with the external world. The accurate pairing of sensation and action, assuming these functions are intact, is dependent on timing and is called sensory-motor timing, one aspect of which is anticipatory timing. Anticipatory timing is essential to successful everyday living, not only for actions but also for thinking. Thinking or cognition can be viewed as an abstract motor function and therefore also needs accurate sensory-cognitive timing. Sensory-motor timing is the timing related to the sensory and motor coordination of an organism when interacting with the external world. Anticipatory timing is usually a component of sensory-motor timing and is literally the ability to predict sensory information before the initiating stimulus.

Anticipatory timing is essential for reducing reaction times and improving both movement and thought performance. Anticipatory timing only applies to predictable sensory-motor or sensory-thought timed coupling. The sensory modality (i.e., visual, auditory etc.), the location, and the time interval between stimuli, must all be predictable (i.e., constant, or consistent with a predictable pattern) to enable anticipation movement or thought.

Without reasonably accurate anticipatory timing, a person cannot catch a ball, know when to step out of the way of a moving object (e.g., negotiate a swinging door), get on an escalator, comprehend speech, concentrate on mental tasks or handle any of a large number of everyday tasks and challenges. This capacity for anticipatory timing can become impaired with aging, alcohol, drugs, hypoxia, infection, clinical neurological conditions including but not limited to Attention Deficit Hyperactivity Disorder (ADHD), schizophrenia, autism and brain trauma (head injury or concussion). For example, brain trauma may significantly impact a person's cognition timing, one aspect of which is anticipatory timing. Sometimes, a person may appear to physically recover quickly from head or brain trauma, but have significant problems of concentration, memory, headaches, irritability and other symptoms as a result of impaired anticipatory timing. In fact, impaired anticipatory timing may cause the person to suffer further injuries by not having the timing capabilities to avoid another accident.

SUMMARY OF DISCLOSED EMBODIMENTS

A method of training a subject to improve anticipatory timing includes presenting the subject with multiple sequences of stimuli, receiving sensor signals associated with responses by the subject to the stimuli, and recording response times in accordance with the sensor signals, wherein the recorded response times are associated with the responses by the subject to the multiple sequences of stimuli, and wherein the response times have an associated distribution. The method further includes analyzing the distribution of response times for the subject to determine variability in anticipatory timing of the subject with respect to the stimuli, and generating a subject feedback signal corresponding to a result of the analyzing so as to train the subject to improve anticipatory timing of the subject. Also disclosed is a system for performing the aforementioned training method.

BRIEF DESCRIPTION OF THE DRAWINGS

Like reference numerals refer to corresponding parts throughout the several views of the drawings.

DESCRIPTION OF EMBODIMENTS

Since it is extremely difficult to measure thinking performance without a movement and since a similar neural network is used for anticipatory timing, cognition and motor timing are linked. Therefore diagnosis and therapy can be performed for anticipatory timing difficulties in the motor and cognitive domains using motor reaction times and accuracy. In particular, both the reaction time and accuracy of a subject's movements can be measured. As discussed below, these measurements can be used for both diagnosis and therapy.

Anticipatory cognition and movement timing are controlled by essentially the same brain circuits. Variability or a deficit in anticipatory timing produces imprecise movements and disrupted thinking, such as difficulty in concentration, memory recall, and carrying out both basic and complex cognitive tasks. Such variability and/or deficits leads to longer periods of time to successfully complete tasks and also leads to more inaccuracy in the performance of such tasks. Some embodiments of the present invention measure such variability or deficits to determine whether a person suffers impaired anticipatory timing. Some embodiments of the present invention use a sequence of stimuli in combination with a feedback mechanism to train a person to improve anticipatory timing.

Sequenced stimuli presented to a subject may include sequences of both predictable and non-predictable (e.g., random or pseudo-random) stimuli. In one embodiment, the non-predictable stimuli are presented to a subject before the predictable stimuli. The stimuli can use any sensory modality. In some embodiments, the stimuli are visual stimuli. In other embodiments, the stimuli are auditory. While other forms of stimuli can be used, the embodiments described here use visual stimuli. The subject's responses may be visual, manual or even spoken. In some embodiments the subject's responses are measured by tracking eye movement. In other embodiments, the subject's responses are measured by a mechanical, piezoelectric or other sensors activated by physical movement of the subject, such as pressing a button. In yet other embodiments, a frontal brain electroencephalographic (EEG) signal (e.g., the "contingent negative variation" signal) is measured during the period before a subject's response. The amplitude of the EEG signal is proportional to the degree of anticipation and will be disrupted when there are anticipatory timing deficits.

Figure 1:
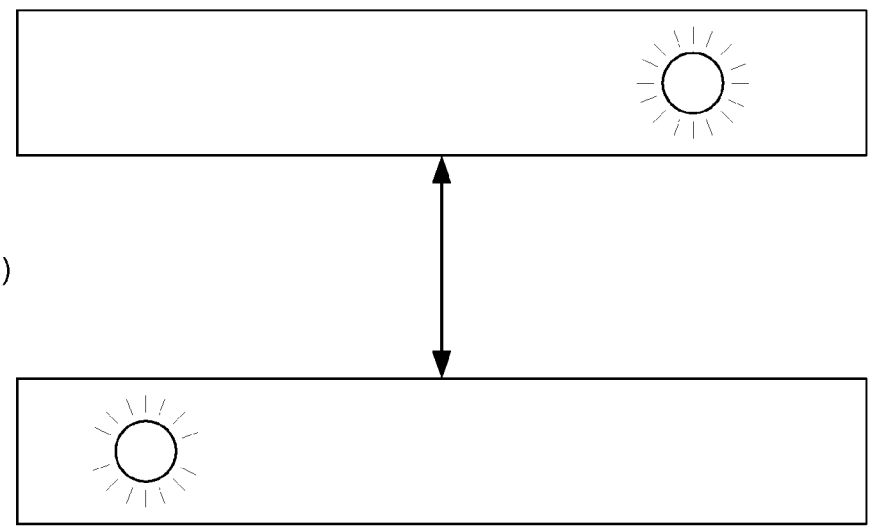
FIG. 1 illustrates a sequence of stimuli presented to a person, in this case two circles that alternately go on and off in a predictable or random fashion.

FIG. 1 depicts a sequence of visual stimuli. The subject's task is to follow the illuminated circle, which will alternate between two locations at a random (non-predictable) or non-random (predictable) rate. In one embodiment the random rate is between 500 msec to 2 sec. The subject may indicate that the circle is illuminated at a particular location by activating a sensor, or by moving his/her eyes to focus on the illuminated circle on the screen. In another example, the subject may indicate that the circle is illuminated at a particular location by controlling the position of an image of an object on a screen using a joystick or other user input mechanism, and may be asked to move the object so as to "catch" a moving object, or to avoid being hit by another object, or to move the object so as to match the movement of a computer generated image, or other similar exercise.

In yet another example, multiple objects, such as images of circles, are displayed in a row or other pattern. The objects are flashed on and off in a predictable or random fashion. Eye movement reaction times are measured by a digital video infrared camera focused on the subject's pupil, operating at a picture update rate of at least 200 hertz. The resulting digital video signal is analyzed by a computer to determine the screen position(s) where the subject was focusing, and the timing of when the subject focused at the appropriate screen position. If feedback is provided, the feedback may be provided by giving the subject a tone, using either open air audio speakers or headphones, or by having the color of the display change when the subject's anticipatory timing is within a normal or desired distribution.

In some embodiments, the stimuli presented to the subject include one or more sequences of non-predictable stimuli. The non-predictable stimuli can be random or pseudorandom sequences. The sequences of non-predictable stimuli cannot be learned and there is therefore no anticipatory timing by the subject. Measurements of the timing of the subject's responses to the sequences of non-predictable stimuli can be used as an internal control. These measurements are measurements of the subject's reactive timing. Subtracting the subject's reactive timing from the subject's anticipatory timing produces the subject's absolute anticipatory timing. By taking numerous timing measurements of the subject's responses to sequences of non-predictable stimuli, a distribution of such timing measurements is generated. The distribution can be graphed or displayed, compared with normative data for a population of other subjects, and the like.

Next, the stimuli presented to the subject also include multiple sequences of predictable stimuli. An initial phase in which the sequences of predictable stimuli are presented is called the learning phase. During the learning phase there is typically a progressive shift toward earlier correct reactions, and thus anticipatory timing. It is noted that in some embodiments, incorrect reactions by the subject are eliminated or not used for purposes of evaluating anticipatory timing. After the learning phase, there should be an anticipatory reaction phase during which the subject's response times are relatively static or fixed. The subject response times during the anticipatory reaction phase will generally be earlier than the initial responses during the learning phase. These response times, herein called anticipatory timing, will also be shorter than the subject's reactive timing to non-predictable stimuli.

By testing the subject with numerous sequences of predictable stimuli and taking measurements of the subject's anticipatory timing, a distribution of such timing is generated. The distribution can be graphed or displayed, compared with normative timing data for a population of other subjects, and the like.

Figure 2A:
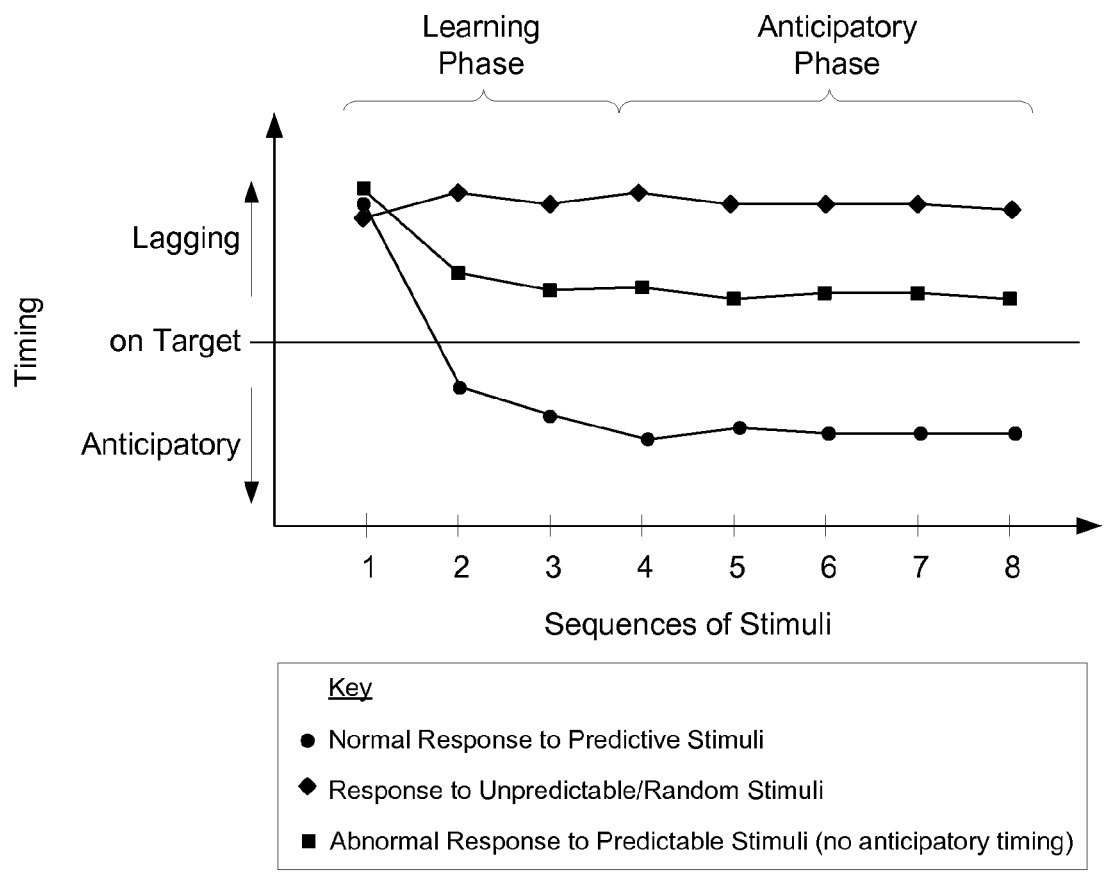
FIG. 2a illustrates a subject's response timing to sequences of stimuli, both for predictable and random stimuli.

FIG. 2a is a prophetic example of a graph of typical response timings to sequences of stimuli, both for predictable and random stimuli. For purposes of this discussion the terms "normal subject" and "abnormal subject" are defined as follows. Normal subjects are typically health individuals whose sensory-motor or anticipatory timing falls within a normal performance range. Abnormal subjects are individuals suffering from impaired brain function with respect to sensory-motor or anticipatory timing.

As represented in FIG. 2a, even normal, health subjects responding to random stimuli (♦) cannot anticipate the exact timing of the stimuli, and thus they lag behind being "on target." In other words, even after a learning phase where the user is subjected to a number of sequences of stimuli, the normal user cannot anticipate a subsequent sequence of random stimuli.

Normal subjects responding to predictable stimuli (●), such as a repeating sequence of visual stimuli, after a learning phase start to anticipate the stimuli before they are presented to the subjects. During a learning phase the normal subjects learn the sequence of stimuli and are then able to anticipate the stimuli during an anticipatory phase. Abnormal subjects (■), however, only slightly improve their response timing after the learning phase and still cannot anticipate the stimuli during the anticipatory phase. In other words, abnormal subjects may improve their response timing during training, but cannot anticipate subsequent stimuli as well as a typical normal subject.

Figure 2B:
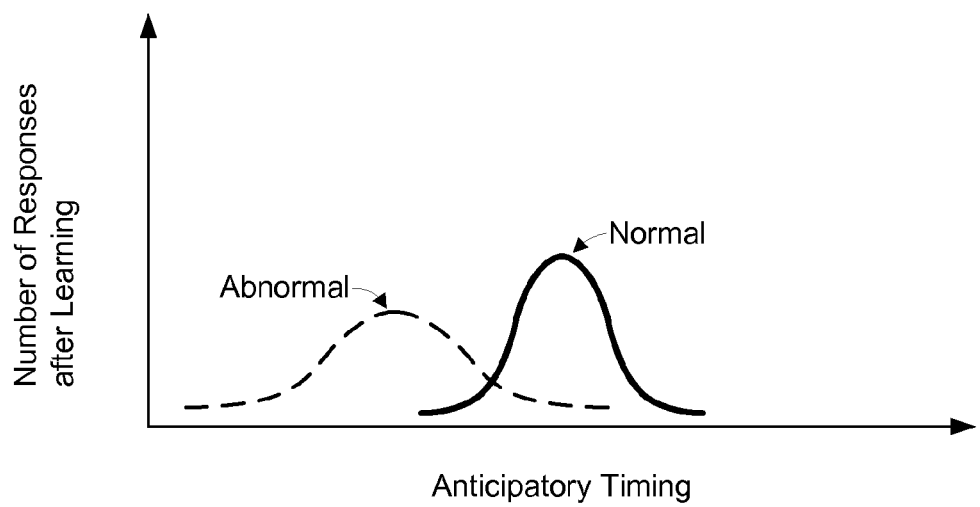
FIG. 2b shows normal and abnormal distributions of anticipatory timing.

FIG. 2b is a prophetic example of the distribution of anticipatory response timing of an abnormal subject and the average anticipatory response timing of a control group of normal subjects. An abnormal distribution of anticipatory response timing is typically slower, on average than the normal distribution. The abnormal subject also typically has more inaccurate responses. Even more significantly, the width of an abnormal anticipatory timing distribution is typically significantly wider than the width of a normal anticipatory timing distribution. In some embodiments, the width of a distribution may be defined as the full width of the distribution at half maximum (sometimes called FWHM). In some embodiments, the width of a subject's anticipatory timing distribution is defined as the variance of the response distribution, the standard deviation of the response distribution, the average deviation of the response distribution, the coefficient of variation of the response distribution, or any other appropriate measurement of the width of the response distribution.

In some embodiments, as described above, the subject's reactive timing is subtracted from the subject's anticipatory timing to produce the subject's absolute anticipatory timing. In some embodiments, this is accomplished by subtracting an average reactive timing value from the anticipatory timing values.

The subject's absolute anticipatory timing distribution can be compared with the absolute anticipatory timing distribution of a control group of subjects. Both the average timing and the width of the timing distribution, as well as their comparison with the same parameters for a control group are indicative of whether the subject is suffering from a cognitive timing impairment.

Figure 3:
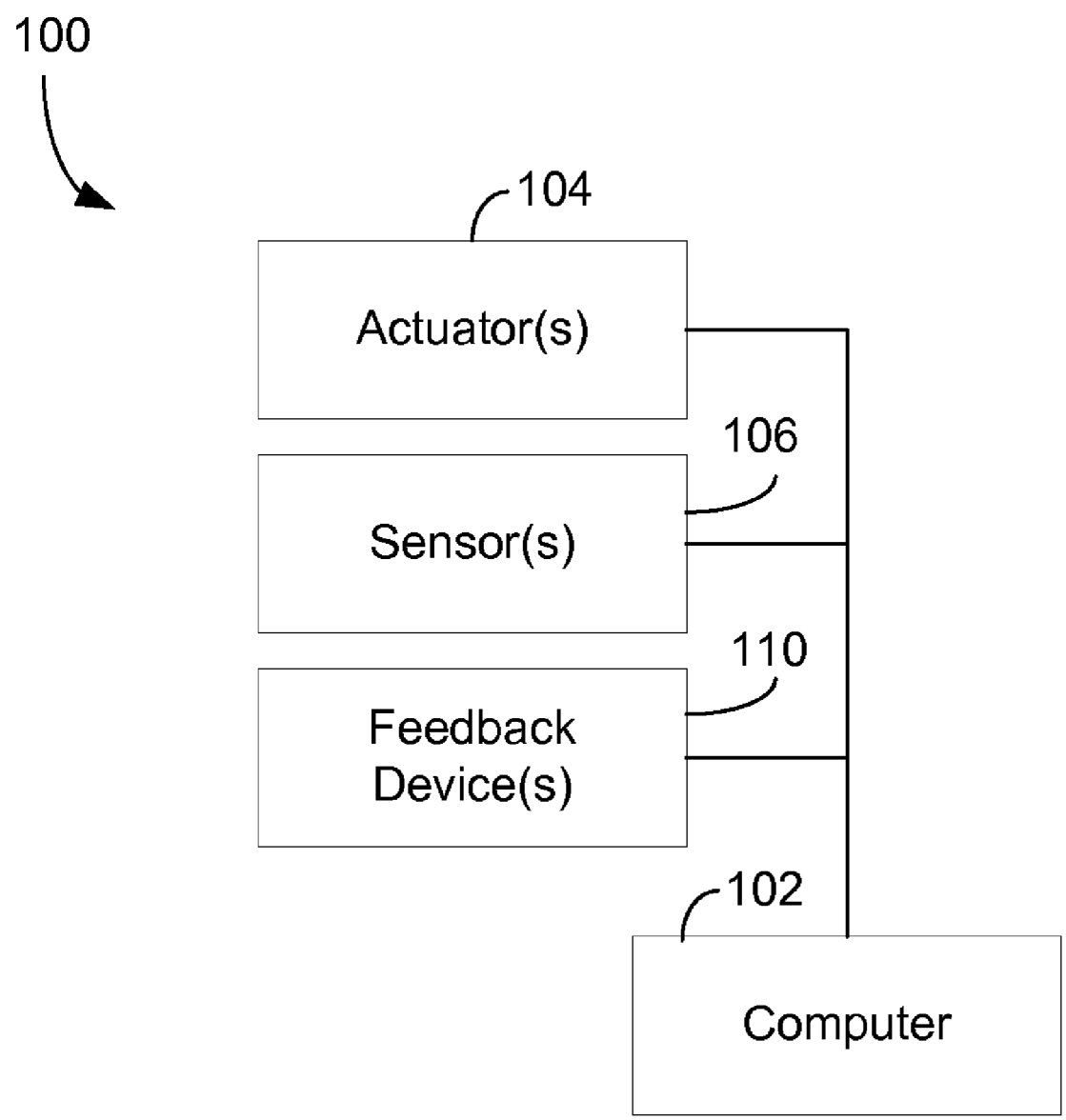
FIG. 3 is a conceptual block diagram of a cognition timing diagnosis and training system.

FIG. 3 is a conceptual block diagram of a cognition timing diagnosis and training system 100. The system includes a computer 102 coupled one or more actuators 104, and one or more sensors 106. When the system is configured for use as a cognitive timing training system, the system 100 may also include one or more feedback devices 110. In some embodiments, feedback is provided to the subject via the actuators 104. The one or more actuators 104 may include a display device for presenting visual stimuli to a subject, audio speakers for presenting audio stimuli, a combination of the aforementioned, or one or more other devices for producing or presenting sequences of stimuli to a subject. The one or more sensors 106, may be mechanical, electrical, electromechanical, auditory (e.g., microphone), visual sensors (e.g., a digital video camera) or other type of sensors (e.g., a frontal brain electroencephalograph, and known as an EEG). The job of the one or more sensors 106 is to detect responses by a subject to sequences of stimuli presented by the one or more actuators 102. Some types of sensors produce large amounts of raw data, only a small portion of which can be considered to be indicative of the user response. In such systems, the sensor or computer 102 contain appropriate filters and/or software procedures for analyzing the raw data so as to extract "sensor signals" indicative of the subject's response to the stimuli. In embodiments in which the one or more sensors 106 includes an electroencephalograph (EEG), the relevant sensor signal from the EEG may be a particular component of the signals produced by the EEG, such as the contingent negative variation (CNV) signal or the readiness potential signal.

The one or more feedback devices 110 can be any device appropriate for providing feedback to the subject. The one or more feedback devices 110 provide real time performance information to the subject corresponding to measurement results, which enables the subject to try to improve his/her anticipatory timing performance. In some embodiments, the performance information provides positive feedback to the subject when the subject's responses, in response to sequences of stimuli, are within a normal range of values. In some embodiments, the one or more feedback devices 110 may activate the one or more actuators 104 in response to positive performance from the subject, such as by changing the color of the visual stimuli or changing the pitch or other characteristics of the audio stimuli.

Figure 4:
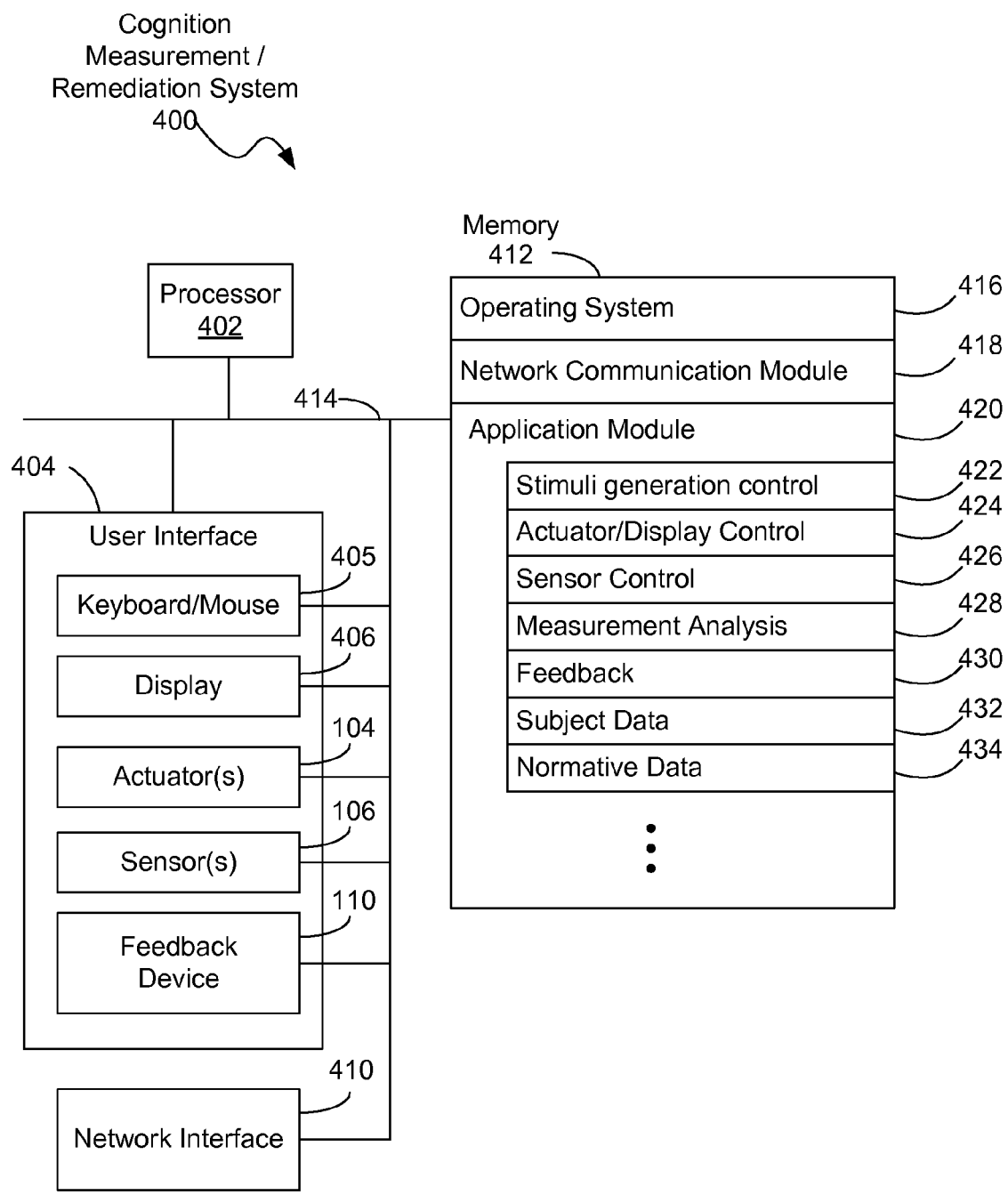
FIG. 4 is a detailed block diagram of a cognition timing diagnosis and training system.

FIG. 4 is a block diagram of a cognition timing diagnosis and training (or remediation) system 400. The system 400 generally includes one or more processors 402, such as CPUs, a user interface 404, memory 412, and one or more communication buses 414 for interconnecting these components. The system 400 may optionally include one or more network or other communications interfaces 410, such as a network interface for conveying testing or training results to another system or device. The user interface 404 includes at least one or more actuators 104 and one or more sensors 106, and may also include one or more feedback devices 110, as discussed above. In some embodiments, the user interface 404 may further include additional computer interface devices such as a keyboard and/or mouse 405 and a display 406 (although the display may one of the actuators 104).

Memory 412 may include high speed random access memory and may also include non-volatile memory, such as one or more magnetic disk storage devices. Memory 412 may include mass storage that is remotely located from the central processing unit(s) 402. The memory 412 stores an operating system 416 (e.g., Microsoft Windows, Linux or Unix), an application module 420, and may optionally store a network communication module 418. The application module 420 may include:

a stimuli generation control program, module or instructions 422, for generating sequences of stimuli, as described elsewhere in this document;

an actuator or display control program, module or instructions 424, for producing or presenting the sequences of stimuli to a subject;

a sensor control program, module or instructions 426, for receiving sensor signals and, where appropriate, analyzing raw data in the sensor signals so as to extract sensor signals indicative of the subject's response to the stimuli; the sensor control program, module or instructions 426 may also include instructions for controlling operation of the one or more sensors 106;

a measurement analysis program, module or instructions 428, for analyzing the sensor signals to produce measurements and analyses, as discussed elsewhere in this document; and a feedback program, module or instructions 430, for generating feedback signals for presentation to the subject via the one or more actuators or feedback devices.

The application module 420 may furthermore store subject data 432, which includes the measurement data for a subject, and optionally may also include analysis results and the like. The application module 420 may also store normative data 434, which includes measurement data from one or more control groups of subjects, and optionally may also include analysis results, and the like, based on the measurement data from the one or more control groups.

Still referring to FIG. 4, in an exemplary embodiment, the one or more sensors 106 include a digital video camera focused on the subject's pupil, operating at a picture update rate of at least 200 hertz. In some embodiments the digital video camera is an infrared camera, while in other embodiments the camera may operate in other portions of the electromagnetic spectrum. The resulting video signal is analyzed by the one or more CPU's 402, under the control of the measurement analysis program, module or instructions 428, to determine the screen position(s) where the subject focused, and the timing of when the subject focused at one or more predefined screen positions.

Figure 5:
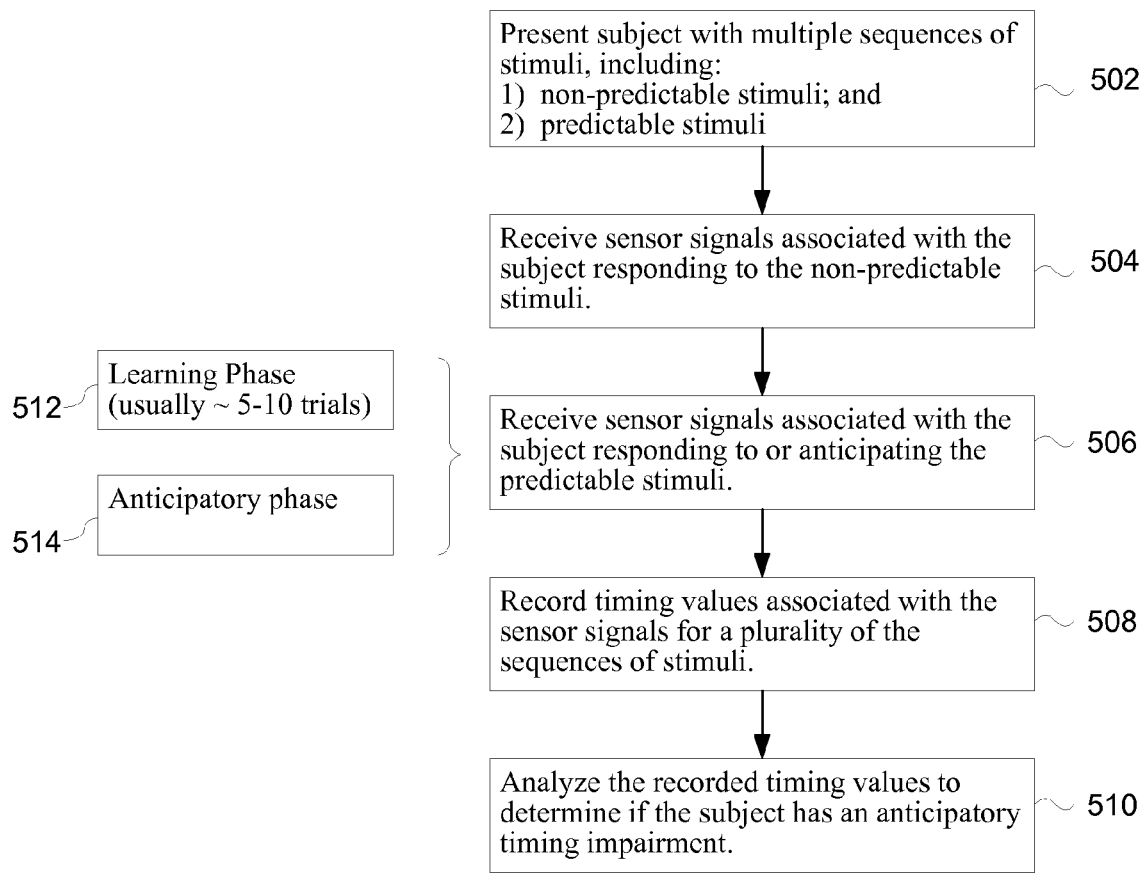
FIG. 5 is a flow chart of a cognition timing diagnosis method.

Referring to FIG. 5, in an embodiment of a method of analyzing a subject's ability to anticipate predictable stimuli, the subject is presented with multiple sequences of stimuli, including sequences of non-predictable stimuli and sequences of predictable stimuli (502). Sensor signals associated with the subject responding to the non-predictable stimuli are received (504). Similarly, sensor signals associated with the subject responding to the predictable stimuli are received (506). In some embodiments, sensor signals associated with the subject responding to the predictable stimuli are received during an initial learning phase (512) followed by an anticipatory phase (514), as described above in relation to FIG. 2a. In some embodiments, the learning phase lasts five to ten sequences of stimuli (trials). Timing values associated with the sensor signals are recorded for a plurality of sequences of stimuli (508). The recorded timing information is analyzed to determine if the subject has an anticipatory timing impairment (510). In some embodiments, a report is generated to present the analysis.

Figure 6:
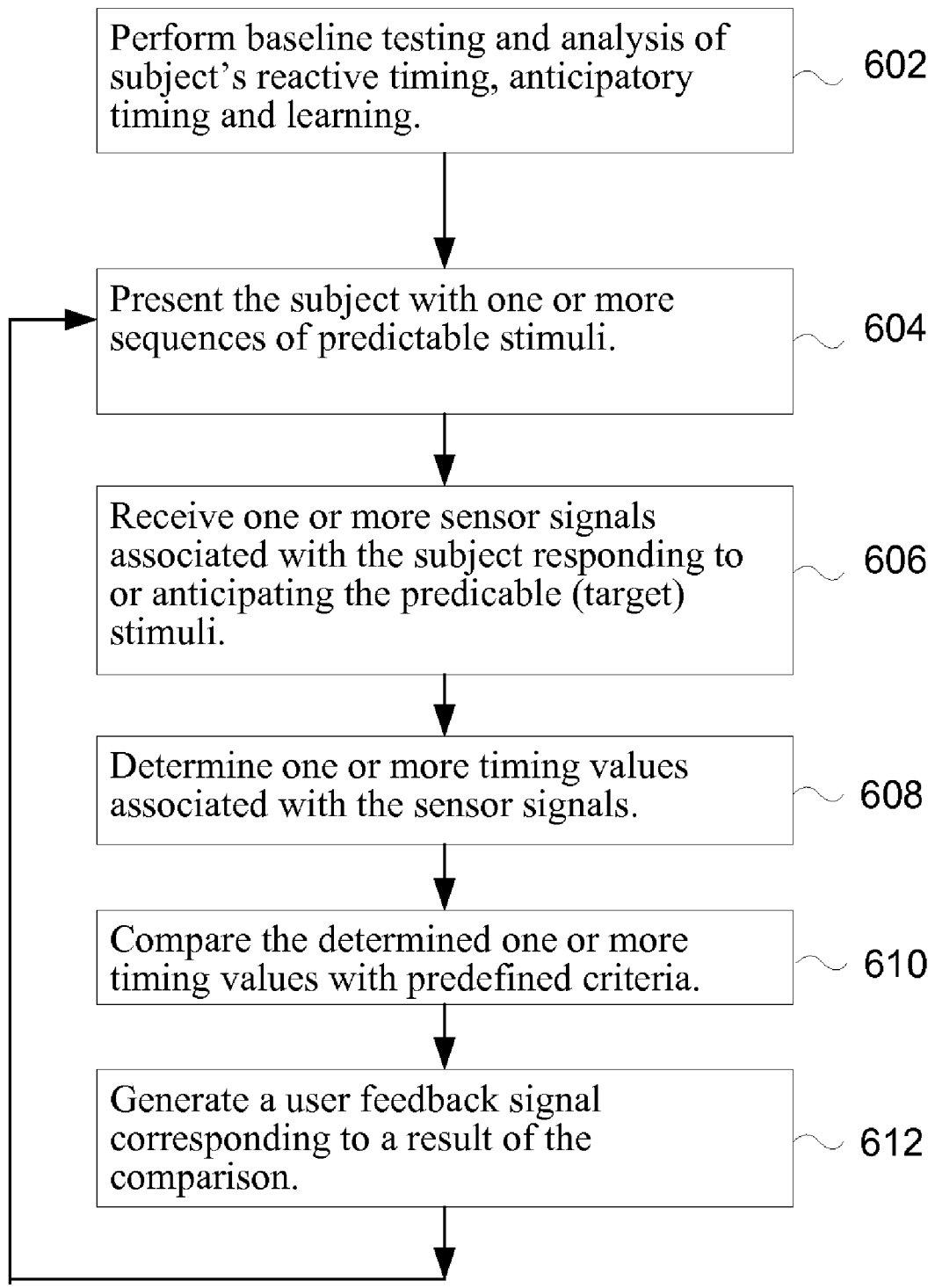
FIG. 6 is a flow chart of an anticipatory timing remedial training method.

Referring to FIG. 6, in an embodiment of a method of training a subject to improve his/her response times to predictable stimuli, the baseline testing and analysis is performed to determine and/or analyze a subject's reactive timing, anticipatory timing and learning (602). This may correspond to a method similar to the one represented by the flow chart in FIG. 5.

Next, a sequence of training steps 604-612 are repeatedly performed so as to help train a subject to improve his/her anticipatory timing. Such training exercises portions of the subject's brain that are responsible for cognitive tasks associated with anticipating events. By focusing the training narrowly on those cognitive tasks associated with anticipating events, appropriate portions of the brain are stimulated, which causes the brain to find ways to improve the subject's ability to anticipate the timing of predictable events.

In some embodiments, the training steps include presenting the person with one or more sequences of predictable stimuli (604) and receiving sensor signals associated with the subject responding to or anticipating the predictable stimuli (606). The sequences of predictable stimuli may include precursor stimuli and target stimuli, with the precursor stimuli providing the subject the information needed to predict the target stimuli. For example, the precursor stimuli may display an arrow pointing to the area in which a visual stimulus will shortly appear. Timing values associated with the sensor signals are determined (608) and compared with predefined criteria, such as baseline data for one or more control subjects (610). Based on the results of the comparison, a subject feedback signal corresponding to the results may be generated (612). In some embodiments, only positive feedback signals are generated, to reward performance meeting predefined or individually determined performance goals. In other embodiments, the feedback signals include negative feedback signals that indicate failure to meet the performance goals. In still other embodiments the feedback signals may include gradations to indicate the extent to which the subject has met or failed to meet the performance goals.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A system for training a subject to improve anticipatory timing, comprising:
    a display to present to the subject multiple sequences of visual stimuli;
    a sensor that produces sensor signals corresponding to responses by the subject to the visual stimuli;
    one or more processors; and
    memory storing one or more programs to be executed by the one or more processors, the one or more programs including instructions for performing a sequence of operations, including:
        presenting to the subject the multiple sequences of visual stimuli;
        recording response times in accordance with the sensor signals, wherein the recorded response times are associated with the responses by the subject to the multiple sequences of stimuli, and wherein the response times have an associated distribution;
        analyzing the distribution of response times for the subject to determine variability in anticipatory timing of the subject with respect to the stimuli; and
        presenting a subject feedback signal to the subject, the feedback signal corresponding to a result of the analyzing, and repeating the sequence of operations so as to train the subject to improve anticipatory timing and reduce variability of the subject responses with respect to the stimuli.

2. The system of claim 1, including a feedback device for providing feedback to the subject in accordance with the subject feedback signal.

3. The system of claim 1, wherein the instructions for analyzing include instructions for comparing the anticipatory timing of the subject with normative data and classifying the anticipatory timing of the subject, including the variability of the anticipatory timing of the subject, as normal or abnormal in accordance with a result of the analyzing.

4. The system of claim 1, wherein the visual stimuli consists of a smoothly moving object, repeatedly moving over a tracking path and the sensor signals are signals derived from video signals monitoring eye movements of the subject; and wherein the determined variability corresponds to how consistently eye movements of the subject visually track movement of the object.

5. The system of claim 4, wherein the sensor comprises a camera operating at a picture update rate of at least 200 Hertz.

6. The system of claim 1, wherein the sensor is mechanical or piezoelectric sensor that responds to a manual action by the subject.

7. The system of claim 1, wherein the instructions for presenting the subject feedback signal are responsive to repeated analysis of the subject's variability in anticipatory timing with respect to the visual stimuli.

* * * * *